United States Patent [19]
Tafur

[11] 3,944,554
[45] Mar. 16, 1976

[54] 4-DESACETOXY-3-HYDROXYVINBLASTINE
[75] Inventor: Susan S. Tafur, Indianapolis, Ind.
[73] Assignee: Eli Lilly and Company, Indianapolis, Ind.
[22] Filed: Jan. 9, 1975
[21] Appl. No.: 539,680

[52] U.S. Cl. .............................. 260/287 B; 424/258
[51] Int. Cl.² ........................................ C07D 471/18
[58] Field of Search ................................. 260/287 B

[56] References Cited
UNITED STATES PATENTS
3,392,173  7/1968  Hargrove .......................... 260/287 B Primary Examiner—R. Gallagher
Assistant Examiner—David E. Wheeler
Attorney, Agent, or Firm—James L. Rowe; Everett F. Smith

[57] ABSTRACT

4-Desacetoxy-3'-hydroxyvinblastine, a novel indoledihydroindole alkaloid obtained in small quantities from *Vinca rosea*, intermediate for the preparation of antimitotic compounds.

2 Claims, No Drawings

4-DESACETOXY-3-HYDROXYVINBLASTINE

BACKGROUND OF THE INVENTION

Several naturally-occurring alkaloids obtainable from *Vinca rosea* have been found active in the treatment of experimental malignancies in animals. Among these are leurosine (U.S. Pat. No. 3,370,057), vincaleukoblastine (vinblastine or VLB) (U.S. Pat. No. 3,097,137), leurosidine (vinrosidine) and leurocristine (VCR or vincristine) (both in U.S. Pat. No. 3,205,220). Two of these alkaloids, VLB and leurocristine, are now marketed as drugs for the treatment of malignancies, particularly the leukemias and related diseases, in humans. Of these marketed compounds, leurocristine is a most active and useful agent in the treatment of leukemias, but is also the least abundant of the anti-neoplastic alkaloids of *Vinca rosea*.

Other dimeric indole alkaloids which have been isolated from *Vinca rosea* but which are less active antimitotically than VLB and leurocristine include leurocolombine (2'-hydroxy VLB), vincadioline (3'-hydroxy VLB), 4-desacetoxy VLB (psuedo VLB), leuroformine and isoleurosine (deoxy VLB "B"). Vincadioline is disclosed in copending U.S. application Ser. No. 466,939 filed May 6, 1974, leuroformine is disclosed in copending U.S. application Ser. No. 469,981 filed May 15, 1974, and leurocolombine is disclosed in U.S. application Ser. No. 469,982 filed May 15, 1974.

SUMMARY OF THE INVENTION

This invention provides a novel indole-dihydroindole alkaloid, 4-desacetoxy-3'-hydroxyvinblastine, having the following formula:

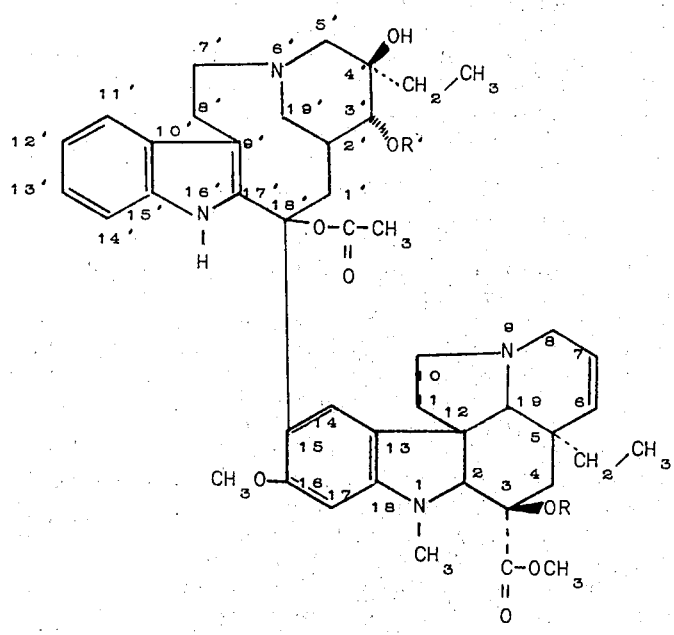

wherein R and R' and H. Also coming within the scope of this invention is 4-desacetoxy-3'-hydroxyvinblastine 3,3'-diacetate represented by the above formula when R and R' are CO—CH₃ (acetyl).

Available chemical and physical evidence indicate that 4-desacetoxy-3'-hydroxyvinblastine has one more hydroxyl than 4-desacetoxyvinblastine itself and that this hydroxyl is in the velbanamine (rather than the vindoline) portion of the molecule. Further evidence indicates that the added hydroxyl is most probably at the 3'-carbon atom as in vincadioline rather than at the 2'-carbon as in leurocolombine.

4'-Desacetoxy-3'-hydroxyvinblastine forms pharmaceutically-acceptable salts with non-toxic mineral acids such as sulfuric, hydrochloric, hydrobromic, phosphoric and the like acids. Treatment of a solution of 4-desacetoxy-3'-hydroxyvinblastine in anhydrous ethanol with 1 percent ethanolic sulfuric acid yields 4-desacetoxy-3'-hydroxyvinblastine sulfate, an amorphous powder, and other salts can be prepared in similar fashion.

4-Desacetoxy-3'-hydroxyvinblastine is prepared according to the following procedure: Defatted leaves of plants containing crude vinca alkaloids; i.e., *Catharanthus roseus* (*Vinca rosea*), previously moistened with aqueous ammonia, are extracted with a water-immiscible solvent such as benzene. The benzene is distilled from the extract in the presence of aqueous tartaric acid. The tartaric acid layer is extracted with a water-immiscible organic solvent and is then made basic by the addition of ammonia. The dimeric alkaloids are extracted from the alkaline layer into an organic solvent, customarily benzene. Evaporation of the solvent yields a mixture of amorphous dimeric alkaoids. The dimeric alkaloid fraction is dissolved in ethanol and the corresponding sulfate salts formed by the addition of ethanolic sulfuric acid. The crystalline mixed sulfate salts are collected and then converted to the corresponding, free bases by solution in water, basifying the aqueous solution and extracting the alkaloids into a water-immiscible organic solvent, customarily methylene dichloride. Evaporation of the solvent yields a mixture of amorphous dimeric alkaloids which are redissolved in methylene dichloride and chromatographed over alumina (CAMAG - Activity III-IV).

The alkaloids are eluted in the following order: leurosine, VLB, des-N-methyl VLB, leurocristine and vinrosidine. Identification of the dimeric alkaloids in the eluant fraction is carried out by standard procedures known to the art, as by thin layer chromatography.

This invention is further illustrated by the following specific example.

EXAMPLE

PREPARATION 4-DESACETOXY-3'-HYDROXYVINBLASTINE

One-thousand five hundred kilograms of dry *Catharanthus roseus* leaf were extracted five times for one-hour periods, using 28 volumes of benzene basified by the addition of 28 percent (w/v) ammonium hydroxide as the extracting medium. The benzene extracts were decanted from fibrous material, combined and filtered. The filtrate was evaporated from aqueous tartaric acid solution which solution was then filtered and the filtrate extracted twice at pH = 3.1 with equal volumes of benzene. The benzene extracts were separated and discarded. The pH of the filtrate was then raised to pH = 6.0 by the addition of concentrated ammonium hydroxide. The aqueous phase at pH = 6.0 was extracted three times with equal volumes of benzene. The benzene extracts were combined and concentrated in vacuo to yield as a residue 4695 g. of a crude alkaloid mixture (VRA). The VRA was dissolved in ethanol and the pH was adjusted to pH = 4.2 with 3 percent ethanolic sulfuric acid. Sulfates of the dimeric alkaloids formed immediately as needles, and crystallization was allowed to continue for two days. The crystals were separated by centrifugation, washed with ethanol and dried. The mixed sulfate salts of leurosine, vincadioline, vinblastine and leurocristine, plus a small quantity of leurosine sulfate were obtained. The salts were converted to the corresponding free bases by dissolving the salts in water, adjusting the pH of the aqueous solution to 8.0 with 14 N ammonium hydroxide and then extracting the water-insoluble bases into methylene dichloride. The methylene dichloride extract was filtered, and the solvent removed by evaporation in vacuo. The resulting alkaloidal residue was chromatographed over 15 kg. of alumina (Activity III–IV, 200 m²/g) using an ethyl acetate-methylene dichloride-water (25:75:04) solvent system as the eluant. Chromatography was carried out in a satinless steel column, 5 cm by 730 cm., at a pressure of 200–400 psi. The alumina-to-charge ratio was approximately 300 to 1. The eluate was monitored at 280 mµ, and fractions were separated based upon the peaks observed in the ultraviolet profile. Fractions were identified containing predominantly leurosine, vinblastine, des-N-methylvinblastine, and leurocristine by thin layer chromatography.

11.75 g. of post-des-N-methylvinblastine, preleurocristine fractions were accumulated i.e., fractions containing more than one dimeric alkaloid occurring after the peak des-N-methylvinblastine fraction and prior to the peak leurocristine fraction, and were converted to the corresponding sulfate salts by treatment with an excess of 1 percent ethanolic sulfuric acid. The sulfate salts were subjected to a gradient pH separation procedure (see U.S. Pat. 3,205,220, Col. 6, line 67 et seq.) According to this procedure, a solution of the sulfate salts in citric acid buffer at pH = 3.4 is extracted with benzene. The pH of the citric acid solution is raised in increments of one-half pH unit, and the resulting aqueous layer extracted with benzene. 4-Desacetoxy-3'-hydroxyvinblastine was found to be present by thin layer chromatography in extracts at pH = 5.4 and 5.9 100 mg. of sulfates (VLB and leurocristine were shown by TLC to be the chief dimeric alkaloid impurities present), recovered from the pH = 5.4 extract, were dissolved in 5 ml. of water and the acidity of the aqueous solution adjusted to pH = 9 by the addition of ammonium acetate. The precipitated alkaloidal free bases were separated by centrifugation, dissolved in 3 ml. of methylene chloride and chromatographed at high pressure in a stainless steel 5/16 inch by 6 meter column packed with neutral alumina [Woelm N-18 (18-30µ)] using a linear gradient of 0–5 percent ethanol in methylene chloride. The column was operated at about 1100 psi with a consequent flow rate of 180 ml/hr. Fractions were collected every 3 minutes after material began to appear in the column effluent as determined by ultra-violet profile. Fractions 30–32 contained 4-desacetoxy-3'-hydroxyvinblastine, as shown by TLC on silica gel using an ether-diethylamine-toluene-methanol (100:5:5:5) solvent system.

Two preparative TLC chromatographic runs were carried out using the above solvent, and 100 mgs. of sulfates from the pH = 5.4 and 5.9 gradient pH extracts. Yields of 4-desacetoxy-3'-hydroxyvinblastine obtained were slightly higher than the yield from the high pressure chromatography procedure.

4-Desacetoxy-3'-hydroxyvinblastine was acetylated in anhydrous pyridine solution using an excess of acetic anhydride. The reaction mixture was allowed to stand overnight at room temperature and the volatile constituents were then removed by evaporation in vacuo. Preparative thin layer chromatography yielded the 3,3'-diacetate (molecular ion = 852) as the major reaction product with traces of a monoacetate also present.

4-Desacetoxy-3'-hydroxyvinblastine (or puedovinblastine diol) prepared and purified by the above procedure has the following physical characteristics, Proton nmr spectrum. The acetate peak is missing. H-17 is shifted to 4.075 δ and the vinyl protons coincide in a multiplet at 5.85 δ. There is a broad multiplet at 5.46–5.78 (clearly different from 4-desacetyl VLB nmr spectrum).

Mass Spectrum
Molecular ion M+ 768 ion fragments at m/e 411,224,102 (characteristic of a 4-desacetoxy vindoline moiety as in 4-desacetoxy VLB)
Ion fragments at m/3 170 and 371 (indicating added hydroxyl to velbanamine moiety of 4-desacetoxy VLB)
Di Acetate Spectra
Ion fragments at m/e 212 and 413 (up 42 mass units from m/e 170 and 371 fragment in 4-desacetoxy-3'-hydroxyvinblastine vindoline moiety). Acetate peaks observed in proton nmr at 1.88, 1.90δ.

4-Desacetoxy-3'-hydroxyvinblastine and its 3,3'-diacetate are useful intermediates for the preparation of C-3 carboxamides, useful as antitumor compounds. These carboxamides are prepared by the procedure more fully set forth in copending U.S. application Ser. No. 446,869 filed Feb. 28, 1974. According to this procedure, 4-desacetoxy-3'-hydroxyvinblastine and hydrazine are reacted in boiling ethanol to form 4-desacetoxy-3'-hydroxyvinblastine C-3 carboxhydrazide. This latter compound is converted to the C-3 carboxazide with sodium nitrite in acidic methanol. Reaction of the azide with methylamine or ethanolamine (or other similar primary and secondary amines) yields 4-desacetoxy-3'-hydroxyvinblastine C-3 N-methylcarboxamide and 4-desacetoxy3'-vinblastine C-3 N-(2-hydroxyethyl) carboxamide for example, active as anti-tumor agents. For such use, the compound or a non-toxic salt thereof such as the sulfate salt is administered orally in the form of capsules or tablets after mixing with suitable pharmaceutical excipients, binders, etc. For parenteral administration, an isotonic solution of a pharmaceutically acceptable salt of a 4-desacetoxy-3'-hydroxyvinblastine C-3 carboxamide is employed. The usual dosage of the amide is in the range 0.1 to 1 mg./kg. of mammalian body weight once a week or more often if desired.

I claim:

1. 4-Desacetoxy-3'-hydroxyvinblastine having the formula

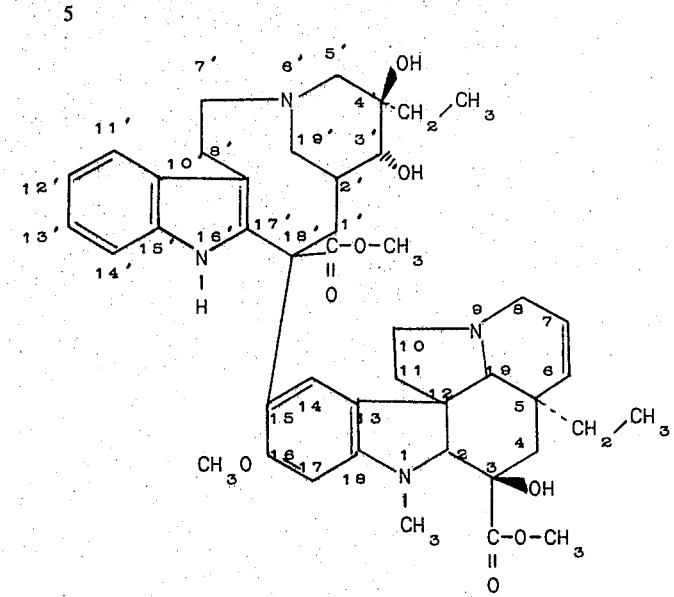

2. 4-Desacetoxy-3'-hydroxyvinblastine having the following physical characteristics:
 proton nmr spectrum;peaks at $\delta$ 4.075, 5.85, 5.46–5.78 (broad multiplet)
 mass spectrum: ions at m/e 768, 411, 371, 224, 170, 102.

* * * * *

UNITED STATES PATENT AND TRADEMARK OFFICE
CERTIFICATE OF CORRECTION

PATENT NO. : 3,944,554
DATED : March 16, 1976
INVENTOR(S) : Susan S. Tafur

It is certified that error appears in the above—identified patent and that said Letters Patent are hereby corrected as shown below:

On the title page, in the title, "-3-" should be -- -3'- --.
Column 1, in the title, "-3-" should be -- -3'- --.
Column 1, line 63, "and" should be --are--.

Signed and Sealed this

Twenty-first Day of September 1976

[SEAL]

Attest:

RUTH C. MASON
*Attesting Officer*

C. MARSHALL DANN
*Commissioner of Patents and Trademarks*